United States Patent [19]
Moore et al.

[11] Patent Number: 6,120,478
[45] Date of Patent: Sep. 19, 2000

[54] SINGLE USE SYRINGE

[76] Inventors: Ian Marshall Moore, 63 Grandview Road, New Lambton Heights, N.S.W., Australia, 2305; Colin Campbell Marshall Moore, 2/230 Falcon Street, North Sydney, N.S.W., Australia, 2060

[21] Appl. No.: 08/817,137
[22] PCT Filed: Oct. 9, 1995
[86] PCT No.: PCT/AU95/00668
   § 371 Date: Jun. 4, 1997
   § 102(e) Date: Jun. 4, 1997
[87] PCT Pub. No.: WO96/11028
   PCT Pub. Date: Apr. 18, 1996
[30] Foreign Application Priority Data
   Oct. 11, 1994 [AU] Australia ............. PM 8718/94
[51] Int. Cl.[7] ....................................... A61M 5/00
[52] U.S. Cl. ............. 604/110; 604/212; 604/217; 604/187
[58] Field of Search ............. 604/110, 181, 604/185, 187, 200, 205, 206, 131, 212–217, 201, 204, 244–247, 908

[56] References Cited

U.S. PATENT DOCUMENTS

| 2,871,857 | 2/1959 | Lipari ............. 128/218 |
| 4,643,199 | 2/1987 | Jennings, Jr. et al. ............. 604/110 |
| 5,263,943 | 11/1993 | Vanderbrook ............. 604/247 |
| 5,773,457 | 6/1998 | Nahoum ............. 514/397 |

FOREIGN PATENT DOCUMENTS

| 5223490 | 10/1990 | Australia . |
| 2632190 | 12/1989 | France . |
| 3827335 | 2/1990 | Germany . |
| 1230543 | 5/1971 | United Kingdom . |
| 2206794 | 1/1989 | United Kingdom ............. 604/247 |
| 2218911 | 11/1989 | United Kingdom . |
| 9204064 | 3/1992 | WIPO . |
| 9419034 | 9/1994 | WIPO . |

*Primary Examiner*—Wynn Wood Coggins
*Assistant Examiner*—Deborah Blyveis
*Attorney, Agent, or Firm*—Edwin D. Schindler

[57] ABSTRACT

There is disclosed herein a single use syringe (1) having a container section (2), a valve section (4) and a hollow needle (4*a*). The valve section (4) contains a one-way valve (40) which allows fluid to flow in only one direction through the valve section (4). The single use syringe (1) may also be provided with locking means to prevent the separation of the container section (2) from the valve section (4). There is also disclosed herein packaging (16, 17) and a carry case (10, 11) in which to store and transport the single use syringe (1).

17 Claims, 6 Drawing Sheets

SINGLE USE SYRINGE

FIELD OF THE INVENTION

This invention relates to medical equipment and, more particularly, to devices for the safe delivery of drugs to the human body by syringes, and to the combination of such syringes and carrying cases therefor. This invention also relates to devices for the safe removal of bodily fluids from the human body.

BACKGROUND OF THE INVENTION

There is a significant risk of cross infection associated with reusable syringes. If not properly sterilised, used syringes can contain a reflux of infected bodily fluids. This risk exists both for reusable syringes which are used to inject drugs and those which are used to remove bodily fluids, such as blood. An accidental needle prick can result in infected blood being injected into the body of a person, possibly resulting in the transferral of a disease.

Many of the drugs used to treat humans, for example, drugs used to treat impotence in human males, are temperature sensitive and need to be kept at a cool temperature. However, those drugs need to be self administered, and are preferably able to be carried on the person of the user. Thus, a need exists for a convenient and safe way of storing, carrying and administering temperature sensitive drugs. Similarly, a need exists for a safe way of storing, carrying and administering a wide range of drugs which are in prescribed fixed doses for self administration, and which may or may not be temperature sensitive.

SUMMARY OF THE INVENTION

There is disclosed herein a single use syringe comprising:
 a container section adapted to contain a predetermined volume of a fluid; and
 a needle section comprising a valve section and a hollow needle, wherein:
  said valve section comprises a one-way valve, and wherein said valve section is adapted to be attached to said container section.

Preferably, said syringe further comprises locking means adapted to prevent the separation of said container section from said valve section after said container section has been connected to said valve section.

There is further disclosed herein a single use syringe in combination with packaging, said packaging comprising:
 a first section adapted to enclose a said container section; and
 a second section adapted to enclose a said needle section;
 said first section comprising a substantially rigid backing portion and a cover portion, said cover portion sealed onto said backing portion around its periphery, said container section being securely housed between said backing and said cover portions; wherein
 said backing and cover portions comprise a weakened portion adapted so that a part of said first section can be torn away to expose a base part of said container section;
 said second section comprising a substantially rigid backing portion and a cover portion, said cover portion sealed onto said backing portion around its periphery, said needle section being securely housed between said backing and said cover portions; wherein
 said backing and said cover portions of said second section comprise a weakened portion adapted so that a part of said second section may be torn away to expose a receiver part of said needle section.

There is further disclosed herein a single use syringe in combination with a carry case, said carry case comprising:
 at least one outer container comprising a lid and a base, said lid and said base forming a space therebetween to house one or more said syringes;
 one or more hinges connecting said lid to said base; and
 one or more clasps adapted to releasably close said container, wherein
 the base of said container is lined with a cooling material adapted to retain a cooled temperature for a predetermined period of time.

DESCRIPTION OF THE DRAWINGS

By way of example only, a preferred embodiment of the present invention will be described with reference to the accompanying drawings, wherein.

Figure 1:
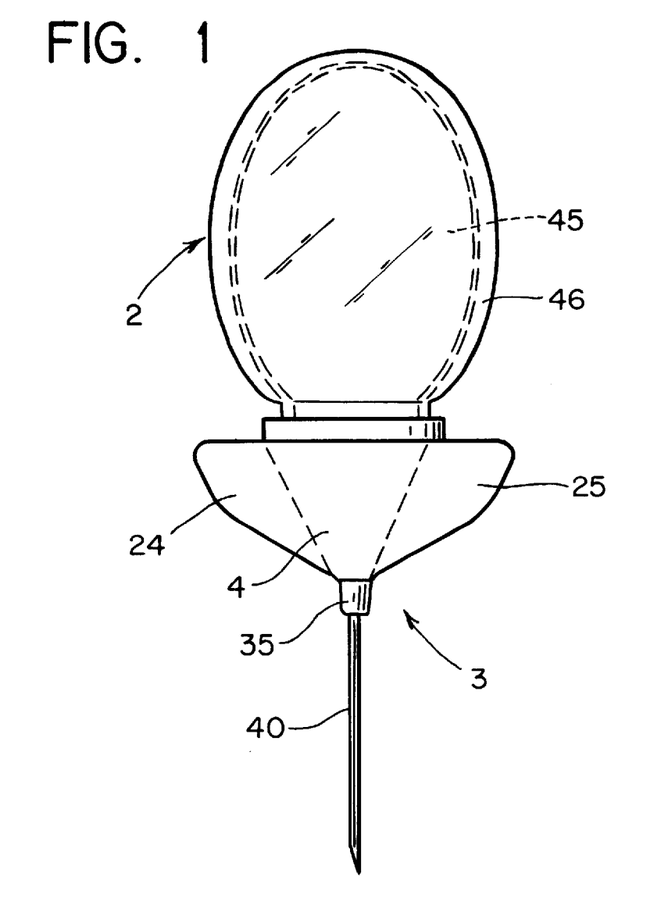
FIG. 1 is a side elevation of an assembled single use syringe.

The assembly and use of a single-use syringe will now be described with particular reference to FIGS. 8–12 and FIG. 1. An example of an assembled syringe can be seen in FIG. 1. The syringe has a flexible walled bubble (2) for containing a fluid such as, for example, a drug. In FIG. 1, the bubble section (2) has been attached to the needle section (3). The needle section (3) comprises a valve section (4) and a hollow needle (4a). The hollow needle (4a) is affixed to the valve section (4) at the needle housing (35). The hollow needle (4a) is preferably made of a hard metal such as surgical stainless steel. The valve section (4) is preferably moulded from a rigid plastics material. The needle section (3) also comprises an upper needle (26) whose function will be described later. The valve section (4) is preferably moulded in two halves, into which the one-way valve (40) and needles (4a and 26) are placed. The two parts are then fused together.

Figure 12:
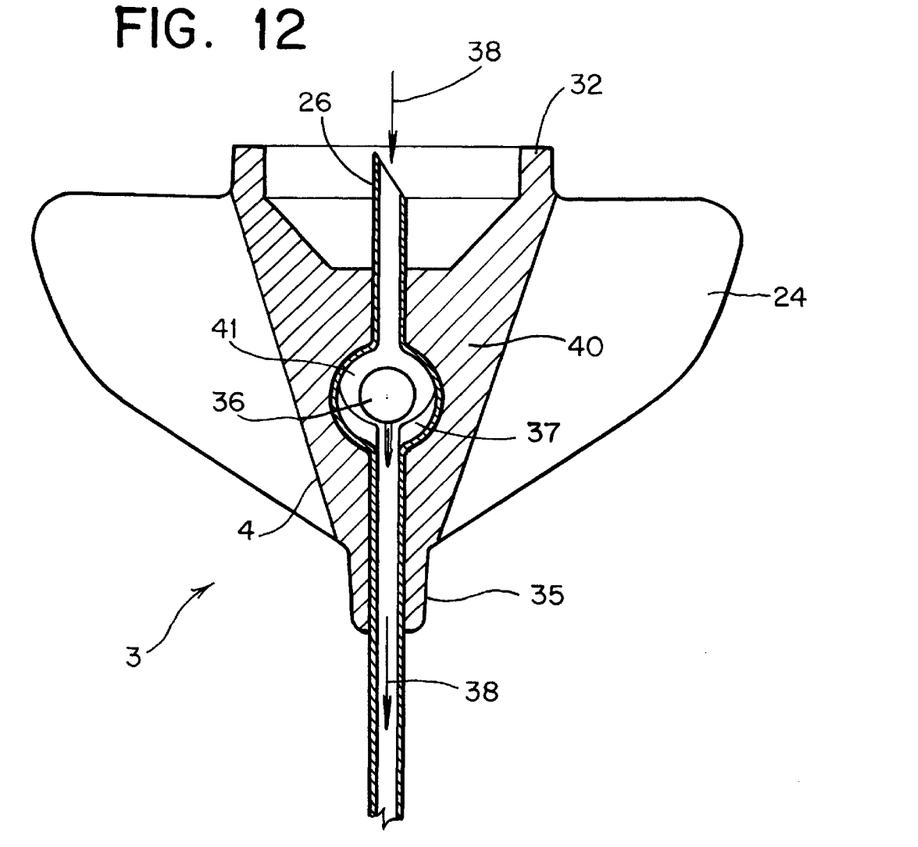
FIG. 12 is a cross-section of the valve section of a syringe.

The valve section (4) comprises a one way valve (40). In the embodiment shown in the drawings, the valve (40) is a ball valve, adapted to allow the flow of fluid only in the direction indicated by arrows (38). The ball (36) sits on a plurality of projections (37), which are provided on the interior space (41) of the valve section (4). When the bubble (2) is squeezed, a flow of fluid flows in the direction of arrows (38), around the ball (36), past the projections (37), out through the hollow needle, and into the body. opening of the space (41), preventing any such reverse flow.

This reduces or prevents the possibility of a reflux of bodily fluids entering the bubble or valve section.

It is to be noted that it is also within the scope of the invention for the valve section (4) to have a one way valve which will only allow flow of fluid up through the hollow needle, and into a container section. The syringe can then be used for the withdrawal of fluids such as blood from a body. The one way valve would prevent any accidental expulsion of fluids out of the container section, lessening the possibility of cross infections occurring due to needle prick injuries.

Furthermore, it is to be noted that it is within the scope of the present invention to utilise any suitable one way valve, for example, a membrane type valve. The ball valve shown in the present embodiment is merely by way of example.

Figures 9, 10:
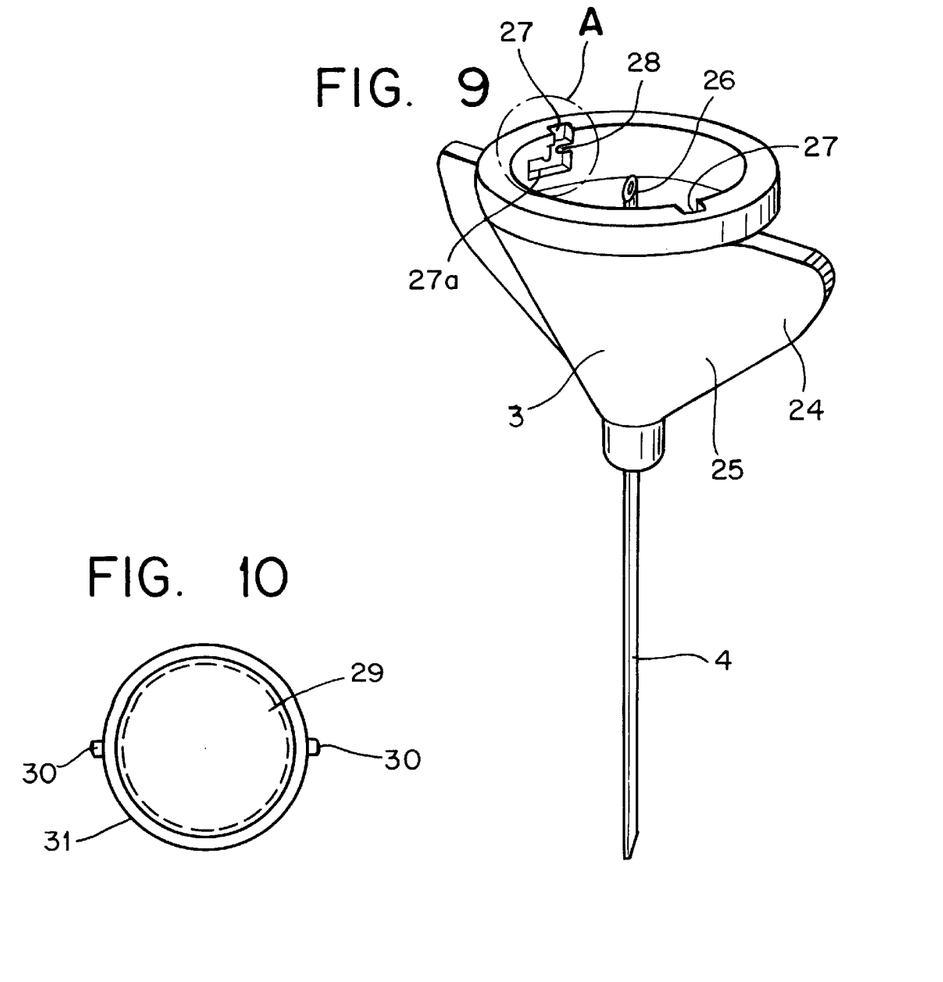
FIG. 9 is a perspective view of the needle section of FIG. 8.
FIG. 10 is a bottom plan view of the base of a bubble section for use with a needle section as shown in FIGS. 8 and 9.

The bubble section (2) shown in FIGS. 1 and 10 is a flexible walled bubble, preferably made of a flexible plastics material (45). The bubble material (45) is preferably transparent, allowing the person using the syringe to see the fluid inside, and check for any visible contaminants.

The bubble (2) is mounted on an attachment base (31) which is attached by the user to a receiving portion of the valve section (4).

The bubble section (2) is sealed across its base (31) by a membrane (29) of a frangible material. The material of the membrane (29) should be strong enough to remain intact throughout the normal handling of the device, such as during transportation, but able to be pierced by the upper needle (26) of the valve section (4) when the device is assembled.

The bubble (2) will normally contain a set dose of a particular drug, ready to be administered (or self administered) to a human body. However, the device may also be used for animals.

As previously mentioned, the device may also be adapted for the removal of bodily fluids. In this case, the bubble, or container portion of the device will initially be empty. For this purpose, the bubble (2) may be replaced by a plunger syringe which has been adapted to connect to the valve section (4), or a vacuum container adapted to draw fluids from a body.

To assemble the syringe, the bubble section (2) and the needle section (3) are partially removed from their packaging (FIGS. 5–7, described below), and then connected, whereupon the upper hollow needle (26), of the valve section (4) pierces the membrane (29).

To ensure that no air bubbles are present in the syringe, the user gently squeezes the bubble (2) until a small droplet of fluid emerges from the end of the needle (4a). The user then inserts the hollow needle (4a) into the body at the desired location, and squeezes the bubble (2). A flow of fluid is then directed down through the one way valve, out through the hollow needle (4a) and into the body.

When the bubble is empty, the entire device can be disposed of. The device cannot be reused, as the valve and bubble sections (2 and 4) have been irreversibly connected. Any attempt to disconnect the two parts will result in the effective breakage of the device. This is an important safety aspect of the subject device.

The subject syringe is particularly suited for containing and injecting drugs to cause and sustain an erection in the penis of a human male. The dosages of such drugs are normally quite low, and can be of the order of 2 ml. For this use, the needle length is to be approximately one-third the diameter of the penis. The bubble section (2) will have a capacity of about 2 ml.

A preferred form of connection between the bubble and the valve sections will be described in more detail below, with particular reference to FIGS. 8–12 and FIG. 1.

Figure 8:
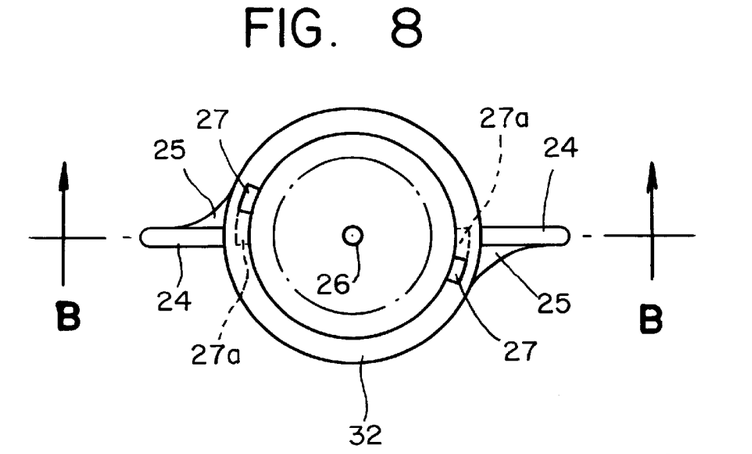
FIG. 8 is a top plan view of a needle section.

The valve section shown in FIGS. 8 and 9 is provided with a circular receiving rim (32). The bubble section (2) as shown in FIG. 10 comprises a circular base section (31) which is sized so as to fit snugly inside the receiving rim (32) of the valve section (4).

The receiving rim (32) of the valve section (4) is provided with a number of slots (27) placed about its circumference. The slots (27) are substantially L-shaped, with a vertical portion, and a horizontal portion (27a). The slots (27) each comprise a flexible lip (28), the function of which will be described below.

The base section (31) of the bubble section has a number of projections (30) provided about its outer periphery. The projections (30) are located such that they will each be aligned over a corresponding slot (27) of the valve section (4), when the bubble base (31) is placed over the valve section receiving part (32).

Figure 11:
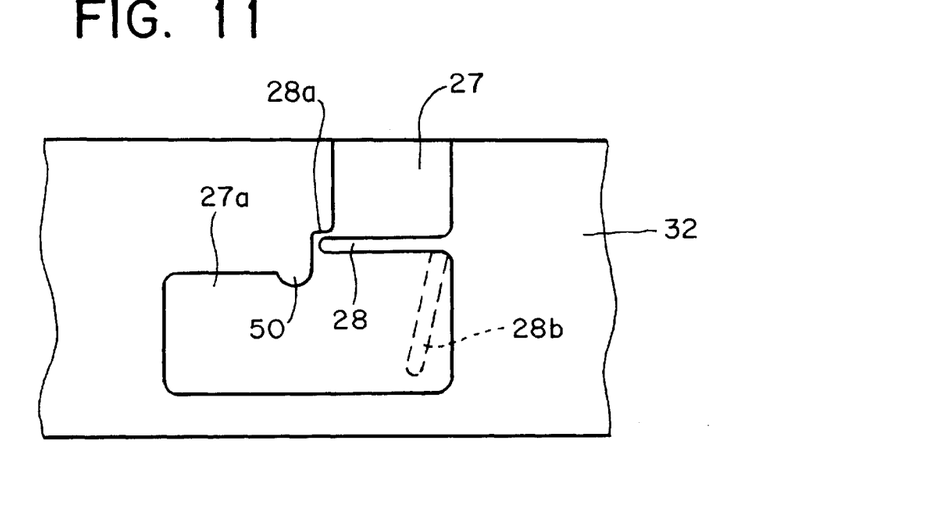
FIG. 11 is a cut-away view of area A from FIG. 9.

To assemble the device, the user places the bubble base (31) over the receiver rim (32) valve section (4) and turns either or both sections around until each projection (30) is aligned with a slot (27). The two sections are then pressed together, until the projections abut the bottom of the slots (27). To reach this point, the user has had to force the projections (30) past the flexible lip (28), which then springs back to its original position. The flexible lips (28) allow the projections (30) to travel into the slots (27) but not out of the slots. The lip (28) bends in the direction (28b), as shown in phantom in FIG. 11. As can be seen in FIG. 11, the abutment (28a) prevents the lip (28) from pivoting upwards. Once the bubble has been attached to the needle section of the device, it cannot be removed. This ensures that the device can only be used once, as once the bubble has been pierced, it cannot be refilled.

When the projections (30) are at the lowermost position within the slots (27), the membrane (29) is pushed onto the upper needle (26), and is pierced. The two sections are then twisted in opposite directions, so that the projections (30) travel to the end of the slots (27a). Optionally, a bead (50) is provided within the slot to further retain the projection in its final location and prevent the assembly from rotating back and forth.

Preferably, one or more radially extending wings (24) are provided on the valve section (4). The wings (24) provide a gripping means to assist the user to press and twist the two sections together.

The wings (24) are preferably adapted so that they assist the attachment of the bubble (2) to the needle section (4), but will break off when used to unscrew or detach the sections. This can be done by providing buttresses (25) which reinforce the wings (24) in the "screwing on" direction, but do not reinforce the wings in the "unscrewing" direction of rotation. Alternatively, the wings (24) may be partially slit at their junction with the valve section (not shown) so that any attempt to pull or unscrew the bubble from the needle section will result in breakage of the wings (24).

It must be noted, however, that the type of fitting described above is only one of a number of possible types of fittings suitable for the syringe device. For example, the bubble section and valve section may be threaded so as to be screwed together (screw fitting not shown).

In this case, a resilient, flexible lip (not shown) is provided on the inside of the valve section receiving rim (32), at the entry point of the screw thread. The lip is depressed upon the insertion and screwing in the bubble base (31), and springs back after the attachment of the sections is completed, to engage the bubble section and thereby prevent or hinder the device's separation. As can be seen in FIG. 1, the bubble section (2) is reinforced along its sides to further assist with the attachment process.

As can be seen in FIG. 12, it is preferred that the upper needle (26) does not protrude above the rim (32) of the needle section (3).

Figure 2:
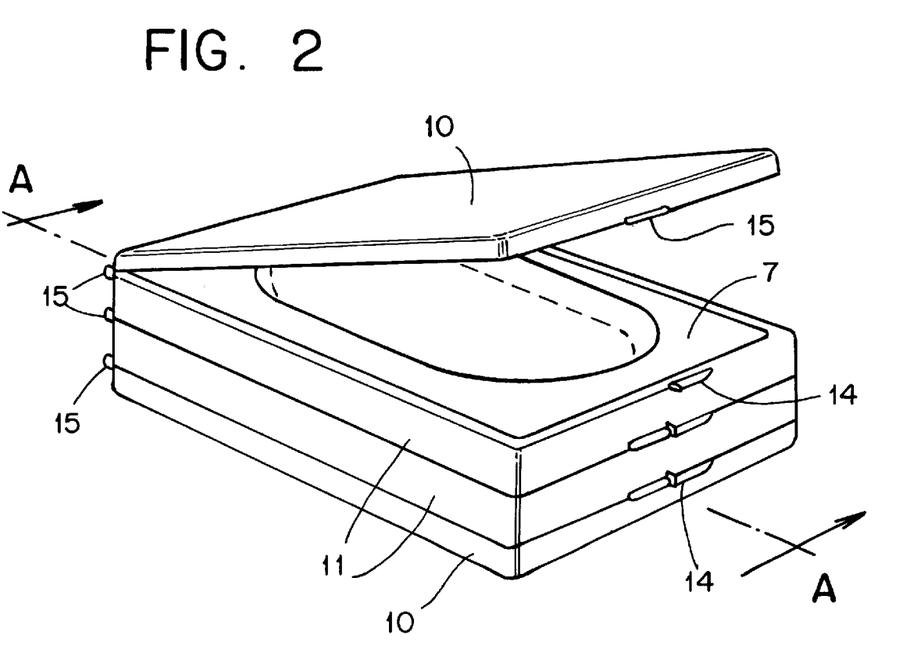
FIG. 2 is a perspective view of a carry case for a single use syringe.
Figure 3:
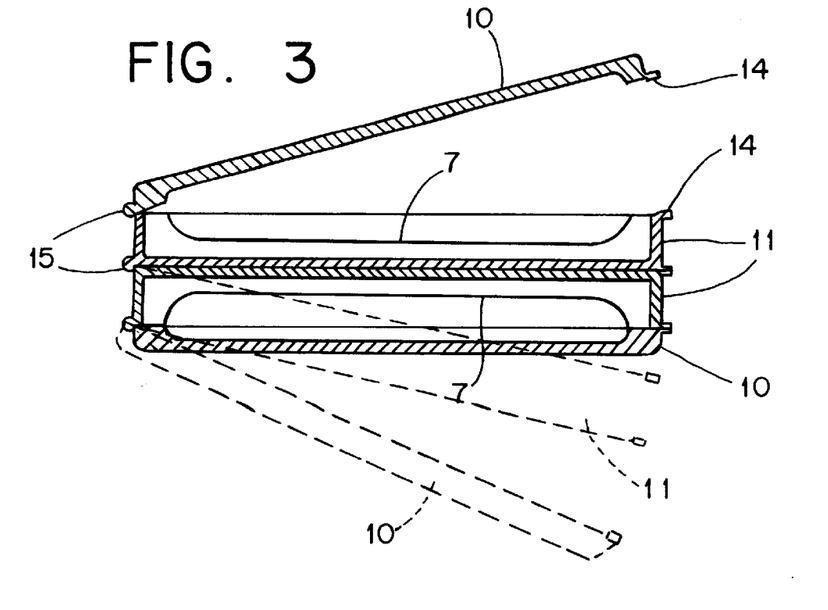
FIG. 3 is a cross-section of the carry case of FIG. 2 taken along line A—A.
Figure 4:
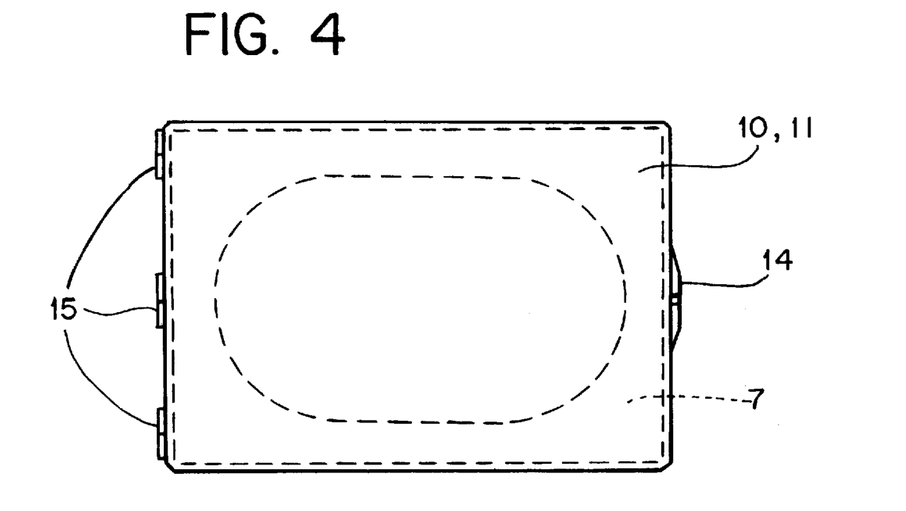
FIG. 4 is a top plan view of the carry case of FIG. 2.

Referring now to FIGS. 2, 3 and 4, the carry case shown comprises at least one lid (10) with a corresponding base portion (11). In the embodiment shown in FIGS. 2, 3 and 4, the carry case comprises two lids (10) and two bases (11). However, the carry case can comprise any number of lids and bases, either stacked one above the other (as shown in FIGS. 2–4), or joined side by side, depending on how many syringes are desired to be carried.

The carry case further comprises a lining of cooling material (7), which is adapted to retain a cool temperature for several hours after being removed from a freezer or refrigerator. The lid (10) may also contain a lining of cooling material (7). As can be seen in FIGS. 2–4, the bases (11) and lids (10) are connected by hinges (15). The hinges may be formed separately and later attached to the carry case, or may be moulded with the base (11) and lid (10) as a one piece structure. Clasps (14) are provided to releasably close the carry case.

Preferably, the carry case is constructed of a rigid plastics material, which will withstand cooling in a freezer or refrigerator and offer protection to the syringes inside it.

The syringes can be stored in the base (11) of the carry case, in an unassembled form, to be assembled by the user in the manner described above. The carry case is particularly suited for the transportation of syringes which contain temperature sensitive drugs. However, it is envisaged that non-temperature sensitive drugs can also be conveniently transported using the carry case. It is also foreseen that instructions for use of the syringe will be attached inside the lid (10) of the carry case.

Figure 5:
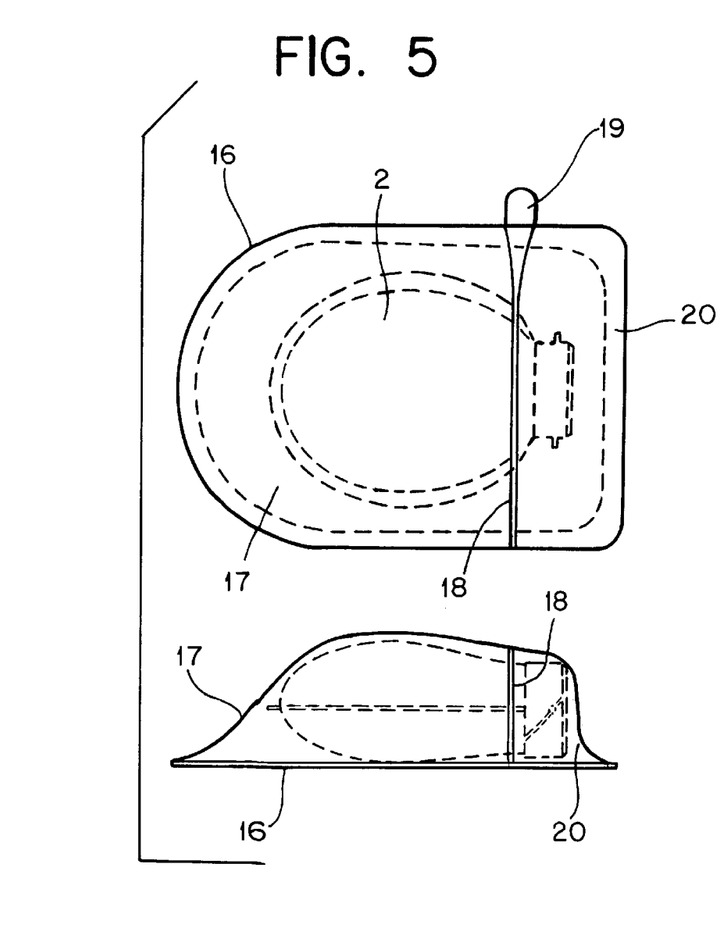
FIG. 5 is a top and side elevation of a bubble section encased in bubble packaging.
Figure 6:
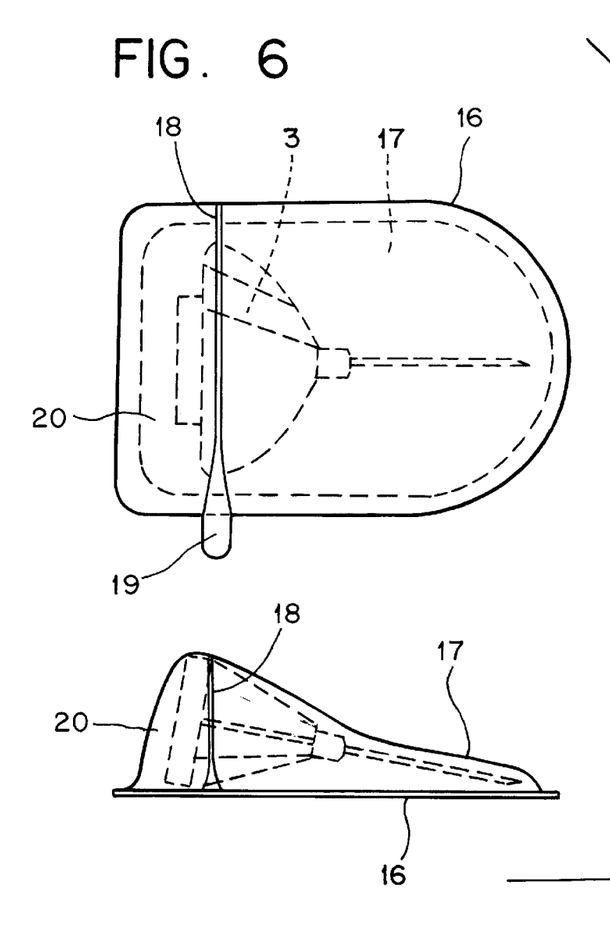
FIG. 6 is a top and side elevation of a needle section encased in bubble packaging.

As can be seen in FIGS. 5 and 6, the syringes are provided in an unassembled form, to be assembled by the user as described. This arrangement has the particular advantage that a drug can be stored in the sealed bubble (2), which is only pierced when the syringe has been assembled and is ready to be used. Furthermore, the user will not have to draw their dose of drug from a separate container into a plunger syringe for self administration.

Referring now to FIG. 5, the bubble section (2) is preferably housed inside rigid contour packaging. The packaging comprises a substantially rigid base (16), over which the bubble is placed. The bubble is sealed against the base (16) by a film (17) of an appropriate packaging material, such as clear plastics material.

Both the base (16) and the film (17) are perforated, or otherwise weakened (18), so that a section (20) of the package can be torn away, exposing the base section of the bubble. Preferably, a tag (19) is provided on the package to assist the user to tear the package along the weakened line.

The needle section (3) is sealed in a similar type of rigid contour packaging. In a similar manner to that described above, a section of the packaging can be torn away (see FIG. 6), revealing the receiving portion of the needle section.

Figure 7:
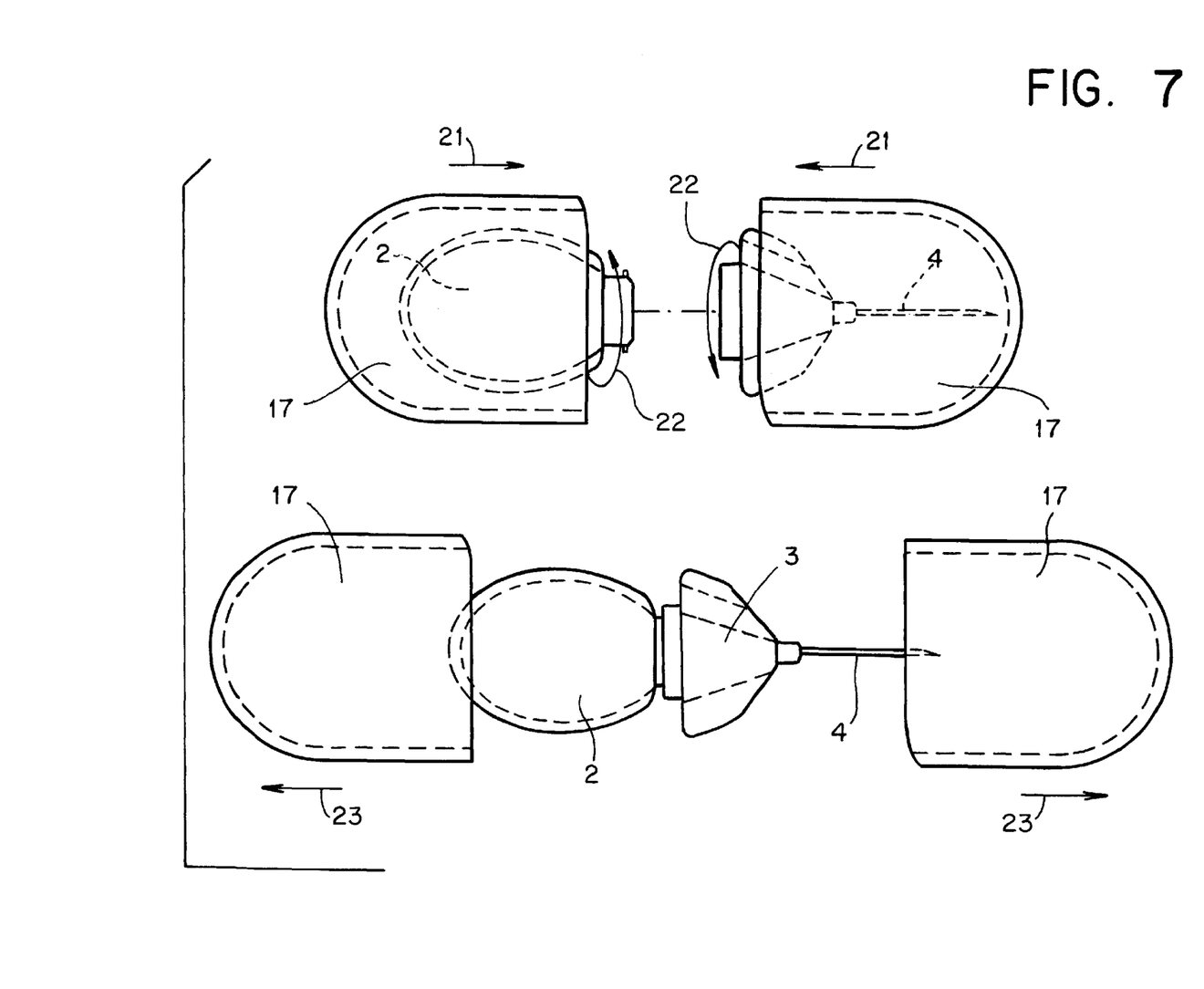
FIG. 7 is a schematic illustration showing the assembly of the bubble and needle sections using the packaging of FIGS. 5 and 6.

Looking now to FIG. 7, the syringe is assembled by pressing together, and then twisting, the exposed ends of the bubble and the needle section. The remaining packaging sections can be gripped to assist with this process. The wings on the needle section also assist by providing a further gripping means. The remaining packaging can then be removed by gripping the mid-point of the syringe, and pulling away both pieces of remaining packaging.

Preferably, instructions, safety considerations and disposal suggestions are printed or stuck on the reverse side of the base portion (16) of the packaging. The packaged needle sections should be able to fit inside the cool carry case for sale as a unit, or can also be supplied separately. The syringe is preferably placed back inside the contour packaging for safe disposal.

Alternatively, the needle and bubble sections may simply be provided in a flexible plastic packaging. Further, the rigid contour packaging may also comprise packing and/or sterilising surgical spirit impregnated with which to swab the injection site prior to injection.

The claims defining the invention are as follows:

1. A single use syringe, comprising:
   a container section;
   a needle section manually attachable to said container section so that said container section is in fluid communication with said needle section, said needle section comprising a valve section and a hollow needle, said valve section comprising a one-way valve for allowing fluid to flow in only one direction through said needle section; and,
   a locking mechanism manually and irreversibly attaching said container section to said needle section.

2. The single use syringe according to claim 1, wherein said container section comprises a flexible walled bubble.

3. The single use syringe according to claim 1, wherein said container section includes a lower membrane for containment of said fluid in said container section prior to use.

4. The single use syringe according to claim 3, wherein said container section comprises a base section attachable to a receiver portion of said valve section, said valve section further comprising an upper needle for piercing said lower membrane of said container section when said container section is attached to said valve section prior to use.

5. The single use syringe according to claim 2, wherein said receiver portion of said valve section includes at least one substantially L-shaped slot, said base section of said container section comprising a corresponding number of projections, wherein said container section is attached to said valve section by inserting said projections into said slots.

6. The single use syringe according to claim 5, further comprising a flap disposed across one of said slots, said flap allowing one of said projections to enter said slot, said flap further preventing the removal of said projection from said slot.

7. The single use syringe according to claim 2, wherein said base of said container section comprises a threaded portion screwable onto a threaded portion of said receiver section of said valve section.

8. The single use syringe according to claim 7, further comprising a resilient flap disposed on, at least, a portion of said receiver section, said resilient flap preventing an unscrewing of said container section from said valve section.

9. The single use syringe according to claim 1, wherein said one-way valve allows a flow of fluid out of said container section and through said hollow needle, said one-way valve preventing a flow of fluid in an an opposite direction.

10. The single use syringe according to claim 1, wherein said one-way valve allows a flow of fluid into said container section through said hollow needle, said one-way valve preventing a flow of fluid in an opposite direction.

11. The single use syringe according to claim 10, wherein said container section comprises a vacuum container for drawing bodily fluids through said hollow needle and said one-way valve, into said vacuum container.

12. The single use syringe according to claim 1, wherein said valve section comprises gripping means for holding said valve means.

13. The single use syringe according to claim 12, wherein said gripping means comprises at least one wing extending from said valve section.

14. The single use syringe according to claim 13, wherein each said wing comprises a buttress for reinforcing said wing when said container section is being attached to said valve section, each said wing being adapted for fracturing when said container section is being detached from said valve section.

15. The single use syringe according to claim 1, wherein said one-way valve comprises a ball valve.

16. The single use syringe according to claim 1, wherein said container section contains a fixed dose of a drug capable of initiating or sustaining an erection of a penis of a human male.

17. The single use syringe according to claim 16, wherein the length of said hollow needle is approximately one-third the diameter of said penis.

* * * * *